(12) United States Patent
Cumming et al.

(10) Patent No.: US 7,357,043 B2
(45) Date of Patent: Apr. 15, 2008

(54) CHEMICAL TRACE DETECTION PORTAL BASED ON THE NATURAL AIRFLOW AND HEAT TRANSFER OF VEHICLES

(75) Inventors: Colin Cumming, Stillwater, OK (US); Eric Towers, Stillwater, OK (US); Mark Prather, Stillwater, OK (US)

(73) Assignee: Nomadics, Inc., Stillwater, OK (US)

( * ) Notice: Subject to any disclaimer, the term of this patent is extended or adjusted under 35 U.S.C. 154(b) by 0 days.

(21) Appl. No.: 11/220,501

(22) Filed: Sep. 7, 2005

(65) Prior Publication Data

US 2007/0056392 A1 Mar. 15, 2007

(51) Int. Cl.
*G01N 1/00* (2006.01)
(52) U.S. Cl. .................................... 73/864.33
(58) Field of Classification Search ............. 73/864.81, 73/864.33, 23.4, 23.2, 25.01; 250/287, 288; 422/91, 93
See application file for complete search history.

(56) References Cited

U.S. PATENT DOCUMENTS

| | | | |
|---|---|---|---|
| 4,045,997 A | 9/1977 | Showalter et al. | ............ 73/23.2 |
| 4,202,200 A | 5/1980 | Ellson | ....................... 73/31.05 |
| 4,896,547 A | 1/1990 | Arney et al. | ............. 73/863.81 |
| 4,964,309 A | 10/1990 | Jenkins | ..................... 73/864.81 |
| 4,987,767 A | 1/1991 | Corrigan et al. | ........... 73/23.36 |
| 5,200,614 A | 4/1993 | Jenkins | ........................ 250/286 |

(Continued)

FOREIGN PATENT DOCUMENTS

JP 2002098384 A * 4/2002

OTHER PUBLICATIONS

AS&E "Z Portal", Multi-View Drive-Through Screening System for Cargo and Vehicles (Relocatable), X-ray system; http://www.as-e.com/products_solutions/portal.asp.

(Continued)

*Primary Examiner*—Hezron Williams
*Assistant Examiner*—Tamiko Bellamy
(74) *Attorney, Agent, or Firm*—Dunlap, Codding & Rogers, P.C.

(57) ABSTRACT

A portal is provided with a detector for detecting trace amounts of substances of interest that may be retained on the surface or interior of a vehicular subject. The portal relies upon the continuous process by which microscopic flakes of dust, dirt, pollen, and other surface and interior contaminants as well as adsorbed analyte media and analyte vapors continuously separate from the surface of vehicular subjects and escape from the interior of vehicular subjects. The portal further leverages the existence of a vehicular thermal plume consisting of a layer of warm air adjacent to the vehicular subject. The warm air rises in the cooler surrounding air and transports the microscopic flakes of surface contaminants, desorbed analyte, and analyte vapors upwardly. The portal capitalizes on this phenomenon by providing at least a partial enclosure with a funnel-shaped collector above the vehicular subject. A low speed flow of relatively dense cool air may be introduced into the portal to buoyantly lift the warmer air of the vehicular thermal plume upwardly. The air stream defined by the vehicular thermal plume and the contaminant particles, analyte media, and analyte vapors therein moves to a trap in the funnel-shaped collector above the portal. The trap cooperates with a detector for detecting the presence of molecules of interest.

24 Claims, 5 Drawing Sheets

U.S. PATENT DOCUMENTS

| | | |
|---|---|---|
| 5,491,337 A | 2/1996 | Jenkins et al. .............. 250/287 |
| 5,585,575 A | 12/1996 | Corrigan et al. ......... 73/863.71 |
| 5,753,832 A | 5/1998 | Bromberg et al. ....... 73/864.81 |
| 5,915,268 A | 6/1999 | Linker et al. ................ 73/23.2 |
| 6,073,499 A * | 6/2000 | Settles .................... 73/864.81 |
| 6,334,365 B1 | 1/2002 | Linker et al. ............ 73/864.81 |
| 6,375,697 B2 | 4/2002 | Davies ........................ 55/340 |
| 6,558,626 B1 | 5/2003 | Aker et al. ................... 422/91 |
| 6,708,572 B2 | 3/2004 | Jenkins et al. ........... 73/864.33 |
| 6,790,249 B2 | 9/2004 | Davies ........................ 55/340 |
| 6,837,657 B2 | 1/2005 | Li et al. ...................... 410/65 |
| 6,840,122 B1 | 1/2005 | Jenkins et al. ........... 73/864.33 |
| 6,848,325 B2 | 2/2005 | Parmeter et al. ......... 73/864.33 |
| 2003/0085348 A1* | 5/2003 | Megerle .................... 250/287 |

OTHER PUBLICATIONS

"Trace Explosives Detection Vehicle Portal", Power Point Presentation SAND2004-4668P, presented Sep. 30, 2004; Frank Bouchier, Sandia National Laboratories, Fact Sheet; http://www.sandia.gov/mission/homeland/factsheets/explosives/vehicle.portal_2005_4688.pdf 2 pages.

Rapiscan Systems "GaRDs Portal" http://www.rapiscansystems.com/portal.html; X-Ray System.

GE "EntryScan3"; pp. 2; http://www.geindustrial.com/ge-interlogix/iontrack/prod_entryscan.html.

Scintrex Trace "VE6000", a.k.a. "Large Vehicle Bomb Detection System (LVBDS)"; http://www.scintrextrace.com/brochures/05-25-2006/VE6000.pdf; 2 pages.

* cited by examiner

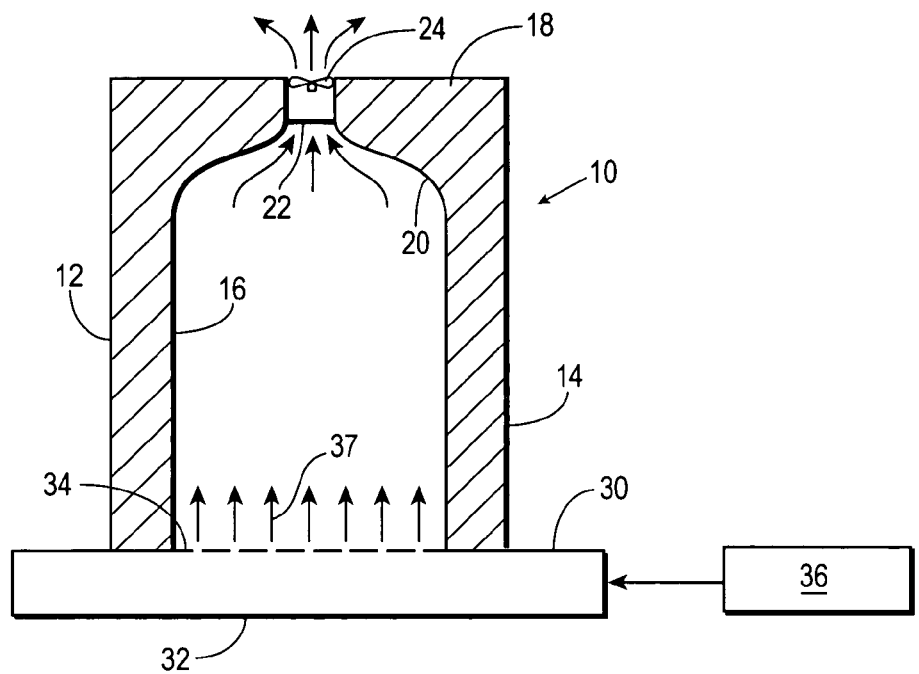
Fig. 3
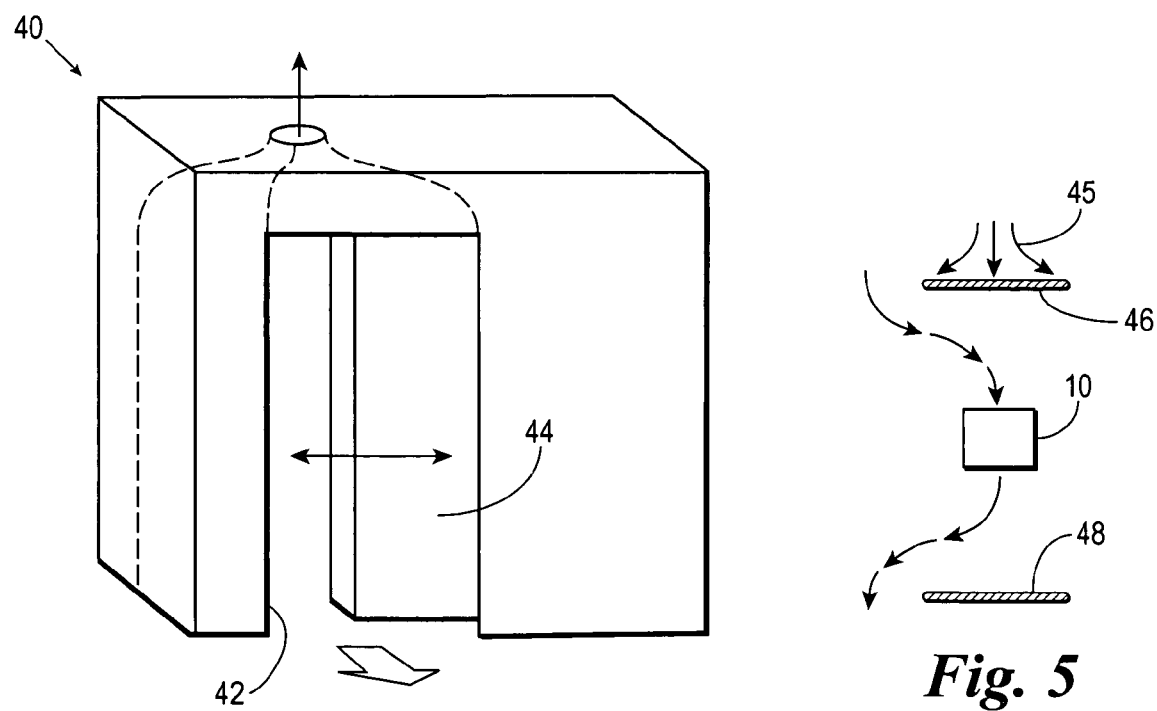
Fig. 4
Fig. 5

CHEMICAL TRACE DETECTION PORTAL BASED ON THE NATURAL AIRFLOW AND HEAT TRANSFER OF VEHICLES

STATEMENT OF FEDERALLY SPONSORED RESEARCH/DEVELOPMENT

Government Funding: W31P4Q-04-C-R166 DARPA

CROSS REFERENCE TO RELATED APPLICATIONS

Not Applicable.

BACKGROUND OF THE INVENTION

1. Field of the Invention

The present invention relates to a portal-type sampling system for sampling the air around vehicles for purposes of detecting trace chemicals present therein.

2. Description of the Related Art

The rise in worldwide terrorism has made it imperative that border traffic security stations and traffic checkpoints screen for concealed explosives as well as performing their normal function of controlling access to certain locations and searching for persons of interest. Experience has shown that concealed explosive devices have been transported onboard vehicles by terrorists on a number of occasions, some of which have resulted in disasters claiming the lives of many persons. Further, the modern terrorist is sophisticated enough to obtain and use plastic explosives, a small amount of which may be sufficient to destroy a building or checkpoint, act as an effective improvised explosive device (IED), or be effectively used to attack military and civilian vehicles and convoys, and which are very difficult to detect.

It is well-known that specially-trained dogs can detect such concealed explosives under the proper circumstances, despite the fact that the concentration of explosive in the air may be as little as a few parts per trillion. Chemical detection devices of exquisite sensitivity have also been developed, based on the principles, for example, of mass spectrometry, ion-mobility spectrometry, or gas chromatography. Very effective devices are shown, for example, in U.S. Pat. No. 5,200,614 that issued to Anthony Jenkins and in U.S. Pat. No. 5,491,337 that issued to Anthony Jenkins and William J. McGann. Commercialized detectors that incorporate the technology of U.S. Pat. No. 5,200,614 and U.S. Pat. No. 5,491,337 typically function by initially rubbing a wipe over an article, such as a piece of luggage, that is likely to carry a trace amount of a composition of interest. The wipe then is placed in an apparatus employing the technology of U.S. Pat. No. 5,200,614 or U.S. Pat. No. 5,491,337, and an air stream is directed through the wipe to transport trace amounts of molecules of interest into the apparatus for detection. A wipe cannot realistically be rubbed across the entire body of a vehicle to test for substances of interest. Therefore, what has been lacking in the prior art is a rapid, convenient, effective means for such sensors to sample the intimate environment of vehicular subjects to screen for concealed explosives.

A hand-held sensor attached to one of the detection devices mentioned above has been used in the prior art to carry out a scan of a vehicle. Such a device is marketed by Nomadics®, Inc. of Stillwater, Okla. under the trademark "FIDO." Some of the technology in this device is disclosed in U.S. Pat. No. 6,558,626. This type of device can be used effectively at vehicle border crossings for detecting the presence of certain explosives, chemical weapons, or narcotics. However, this prior art device would be very time-consuming when applied to the many thousands of vehicles, which pass borders and checkpoints each day, and would be perceived as an intrusive approach which would be likely to elicit objections if used on a significant proportion of those vehicles.

Less intrusive means of screening for concealed explosives have been proposed. As explained in U.S. Pat. No. 6,073,499 issued to Settles, many of these proposals are fundamentally flawed in assuming that the proper method for sampling vapors and particles is to disturb those particles horizontally, or vertically downward. As eloquently explained by Settles, rising from human subjects is a thermal plume. Efficient collection of particles and vapor from a human subject should be performed by leveraging this thermal plume.

Similarly, although not taught by Settles, nor demonstrated in the art, rising from most operating vehicles is a thermal plume. This plume carries dirt, dust, pollen, other particles, and vapor both from the surface of the vehicle and from the interior of the vehicle. This plume has a substantially larger volume than that produced by a person and typically rises much faster than that produced by a person.

Settles references U.S. Pat. No. 4,964,309 issued to Jenkins et al. and observes that particle and vapor sampling systems for human subjects based on air-curtains dilute samples as much as 100,000-fold, that the flow rate cannot be effectively reduced, and that Jenkins solution is "saloon-doors" which make contact with the body and which through suction sample air from intimate contact with the subject. There are several practical problems with a contact solution for sampling from vehicles. Nevertheless, the dilution problem is acute for any particle and vapor collection system, especially when such collection is from a large object, instead of the relatively small object, a person, contemplated in Settles.

Settles expresses that the referenced and above-described prior art perceived a need to strip, scrub, or otherwise dislodge explosive vapors and/or particles from the skin and clothing of human subjects. These vapors and/or particles are presumed to be stagnant and to require active disruption and removal in order to provide a sufficient signal to an explosives-detection analyzer. Further, Settles notes that air currents used in the prior art for purposes of dislodging particles from human subjects are generally oriented horizontally with respect to the vertical orientation of a standing human subject, or at least are not oriented vertically.

As does Settles, we observe that the prior art for sampling portals that avoid physical contact, whether for sampling from human subjects, vehicles, or other subjects, rely upon the movement of very large quantities of air compared to the thin layer of air surrounding the subject. This leads to a very great dilution of the chemical traces released by a subject with concealed explosives. Given such dilution, the task of detecting a vanishingly low concentration of explosive or other chemical trace in a large mass of air becomes essentially an impossible one. Further, the prior art devices generally sample only a small portion of the airstream they create. Since available explosive analyzers can accept only a very small sample size, most of the generated airflow is not examined at all for the presence of trace explosives. Solid particulates are not specifically sampled or, if they are, they are subsequently boiled off to present a gaseous sample to the chemical analyzer. This heating must be done carefully to avoid decomposing the very compounds one is looking for.

Settles notes that the prior art recognizes that some combination of explosive vapor and/or particulates is or may be involved in the proper functioning of an explosive-detection portal. It is further asserted that such portals have broader applications, i.e. in drug and hazardous-materials detection as well. Finally, it is noted that the functions of explosive detection and metal detection, as for concealed weapons, may be integrated into a single portal-type device.

However, neither Settles nor the prior art addresses the additional difficulties of sampling from vehicles. First, the fluid dynamics of a portal large enough to contain a vehicle is more complicated that the fluid dynamics of a small portal containing a human subject. The shape of a vehicle is typically vastly more disturbing to the flow of heated air around it, and substantially complicates the flow pattern in the portal. The temperature of the vehicle, especially in and around the engine compartment is substantially higher than that of a typical human subject, producing both more and hotter thermal plume than for a human subject. This plume rises more rapidly and can thereby more readily induce turbulence in its own motion. Thus we find that the prior art does not adequately teach the efficient capture of particles and vapors from a vehicle.

Further, in Settles, we find teachings related to the emission of skin particles by human subjects. As is evident to one knowledgeable in the art of many fields, including machinery, metal working, and biology, vehicles do not have an epidermis, and do not release flakes of skin into the environment. However, as one knowledgeable in the art of forensics knows, the exterior surface of most objects, perhaps especially vehicles, is covered with dirt, dust, pollen, adsorbed particles and vapors, and other "contaminants" that are characteristic of the environment and materials to which the vehicle has been exposed. These contaminants are constantly exchanging with the environment so that at any instant, contaminants that were previously on the vehicle's surface are liberated into the environment near the car, especially to the layer of air that flows to form the vehicle's thermal plume. Similarly contaminants from the environment are constantly arriving at and adsorbing to the surface of the vehicle. Thus, although the mechanism is different from that of human subjects, a vehicle is constantly exchanging contaminant material with its local environment.

We find, as does Settles that the role of the exchange of these contaminants for detecting trace contamination is not adequately taught in the prior art. Further, we find no evidence in the prior art that the exchange of contaminants between the surface of a vehicle and its surroundings has been taught. Since the feasibility of detecting materials of interest is directly related to capturing the material and passing that material to sensing device, clearly accounting for the vehicular thermal plume and the exchange of contaminants with the environment is a substantial component of successfully screening vehicles.

Finally, we find in the market a dearth of products suitable for the detection of vapors or particles of substances of interest. At this time, vehicle screening portals for radiological detection are essentially the only screening options available. Sandia National Laboratories has demonstrated a drive-through trailer, roughly the size of an ISO container, which contains a shroud that is lowered onto the driver-side window of an automobile and which draws air through the shroud to a sampling apparatus. In all cases, the vehicle is driven into the portal and stopped. For radiological detection, the driver and other occupants are required to leave the vehicle. For the Sandia screening device, roughly two to three minutes is expended positioning the vehicle to be properly fitted by the shroud and then an additional 30 seconds is required to sample vapors. In all cases, the current art shows no evidence of drive-through vehicle screening portals nor of portals that can be passed in very short time, such time necessary to satisfy the throughput requirements of a border crossing or a traffic checkpoint.

SUMMARY OF THE INVENTION

The following discussion is based on Applicants' understanding of the underlying theories involving the invention at this time. The subject invention is based partly on the premise that the art of explosive-detection portals for vehicular subjects may be substantially improved by taking proper account of the thermal behavior of the air surrounding the vehicle, and of the natural particulate field generated by the continuous exchange of contaminants on the vehicle surface with the environment, especially the air immediately surrounding the vehicle. As will be shown below, such consideration is central to the effective detection of concealed explosives or other substances on the vehicle. Further, active stripping, scrubbing, or other removal of trace explosives from the vehicle by mechanical means or air-jet impingement is either unnecessary, insofar as this function is automatically performed by the natural behavior of the vehicular thermal plume itself, or only becomes necessary under such circumstances that the natural signal produced by the vehicle is too weak to detect. The concept of a "stagnant boundary layer" of explosive vapor on or near the vehicle, as described in the prior art, is actually not physically possible within the context of the known behavior of the vehicular thermal plume. In contrast with the horizontal orientation of air currents in the preponderance of the prior art, the subject invention takes advantage of the natural orientation of the thermal plume of an operating vehicle, or of a vehicle which is not operating, but has been standing in a heated or sunny environment, which, as discussed below, is vertical and upward. The prior art thus introduces airflow patterns at direct variance with the natural tendency of the convective airflow about the vehicle, leading to gross inefficiencies in the collection of a concentrated sample of air from the intimate environment of the vehicle.

The present invention is based on the inherent thermal and aerodynamic characteristics of the vehicle, and secondarily on the presence of a large number of particles and/or vapor in the air surrounding the vehicle. An operating or heated vehicle is normally several degrees warmer than the surrounding atmosphere (50 C being reasonable on the surface of the vehicle vs. 24 C room temperature). This causes continuous thermal convection to occur from the vehicle to the surrounding atmosphere. In fact, this circulation is both necessary and encouraged in internal combustion engines to ensure that the engine does not overheat. This fact is well known to one practiced in the art of internal combustion engine design or vehicle design.

The air heated by the vehicle, being warmer and less dense than the surrounding air, rises naturally according to Archimedes' Principle. This generates a boundary layer. For a vehicle, the boundary layer begins at the tires or wheels, which are heated by friction with the road surface when operating or by conduction from a heated road or parking surface when stationary, and travels up the sides of the vehicle, growing thicker and faster as it moves. The flow continues upward and near the upper surfaces of the vehicle this boundary layer detaches and continues its buoyant upward motion, forming the vehicular thermal plume. The vehicular boundary layer and plume are observed to form in about the same manner despite wide variations in vehicle height, weight, paint, etc.

It is thus essential to the present invention that the air in contact with the vehicle is not normally stagnant, but is in a constant state of upward motion. Moreover, the very nature of the motion of the vehicular boundary layer is such that every location on the surface of the vehicle contributes to it. Thus any location where explosives might be concealed all contribute to the buoyant airstream which eventually rises above the vehicle to form the thermal plume. In fact, heated air escaping the interior of the vehicle, whether forced out by the action of an integrated HVAC system, escaping due to the same thermal plume production process occurring on the interior of the car, or being drawn out by natural airflow around the car, also contributes to the plume. Traces of explosives concealed anywhere on or in the vehicle thus migrate naturally upwardly and end up in the thermal plume.

The subject invention operates on the principle that sampling desirably encompasses the entire vehicle in order to ensure that concealed explosives are not overlooked. The vehicular thermal boundary layer accomplishes this task naturally, so that one need only collect the thermal plume rising naturally above a subject vehicle to have a highly-concentrated sample from all locations on the vehicle. Moreover, insofar as this task is accomplished naturally by the vehicular thermal plume, it is highly undesirable to dilute and/or diffuse the plume by artificially-induced air currents, as is done in essentially all art prior to Settles in this field.

The subject invention also takes advantage of certain facts that are well known in the non-analogous forensic arts, namely, that vehicles exchange contaminants in the interior and on their surfaces with their surroundings. As noted by Settles, humans emit large quantities of skin flakes, which are suitable particles and carriers of materials of interest and coat nearly any object brought near the human subject. Thus, as can be demonstrated forensically, a human exposed to the compound of interest will give off skin flakes in copious quantities, some or all of which are contaminated with the compound of interest. These flakes will contaminate the environment of the human, including the interior and exterior of a vehicle that the human touches or occupies. Thus, the skin flakes described in Settles represent one component of the contamination on and in a vehicle which are collected by the subject invention.

The particles and/or vapor released by the vehicles are immediately caught up in the upward motion of the vehicular boundary layer, since their settling speed is typically only 1 mm/sec to, at most, 1 cm/sec.

Accordingly it is highly desirable to collect the rising warm air in the vehicular thermal plume and extract the solid particles and/or vapor it contains, rejecting the air and retaining only the small solid sample with adsorbed trace explosives. Both the vapor not retained and the highly concentrated sample is then presented directly to an appropriate device for analysis and detection, e.g. the instrument described in U.S. Pat. No. 6,558,626. Furthermore, concealed narcotics and other hazardous materials or controlled substances may be detected in the same manner, and a human mitochondrial DNA sample may be extracted from the captured skin-flake sample.

It is important to establish that although the following detailed description is framed in terms of the detection of concealed explosives, this invention has broader and more general applications as well. Specifically, the principles disclosed here may similarly be used to detect other illegal, dangerous, forensic, diagnostic, or otherwise interesting substances concealed upon or inside the vehicle, such as contraband drugs, incendiaries, money, and chemical/biological warfare agents. Further, it is possible with the invention disclosed here to collect a small sample of human particles and/or vapor shed by subjects passing therethrough, from which a human DNA sample can be extracted for purposes of DNA typing of individuals. One embodiment of the presently-disclosed invention may be used to detect trace biological signals emitted by the human body. Trace biological signals include an excess or shortage of proteins, chemicals, and other markers; viral or bacterial contaminants; and breakdown products of these items (e.g. formaldehyde from cancerous cells). These signals can be keyed to the subject's state of health, thereby allowing any of a wide variety of diseases to be diagnosed without direct physical contact, or for the subject's state of mind to be ascertained, perhaps to select agitated persons for further questioning. Changes in the subject's state of mind can be measured based on alkalinity or basicity, which are normally detected as "galvanic skin response," a slight change in the chemistry of the skin. This change is also transferred to emitted skin flakes and to other vapors and particles emitted by the subject. The present invention may be used to detect traces of controlled nuclear substances, such as Uranium, which are difficult to detect by traditional radiation detectors. Finally, the invention may be used to detect trace vapors and particles from radiation shielding, which may be preventing the successful detection of controlled nuclear substances. In short, the invention is suitable for detecting target substances and is not preferential for any particular substance or class of substances.

The collection of the vehicular thermal plume without dilution by extraneous air is accomplished by an open, drive-through portal with an overhead collector, beneath which vehicular subjects may or may not be required to pause for a few seconds. This collector may have an inverted, contoured funnel shape, terminating in a filter, trap, or particulate separator and a single fan or blower which draws the air of the plume through the collector. The filter, trap, or separator may be any one of several different devices including 1) a mesh filter-type separator, 2) a cyclone-type separator, 3) an impingement/particle-inertia-type separator, 4) an electrostatic precipitator, 5) a cold trap, or some other device capable of functioning as a particulate separator. Likewise the explosive, narcotic or other chemical detector to which the resulting sample is presented may be a prior art detector, such as the detectors disclosed in U.S. Pat. No. 5,200,614 or U.S. Pat. No. 6,558,626, the disclosures of which are incorporated herein by reference.

BRIEF DESCRIPTION OF THE DRAWINGS

FIG. 3 is a cross-sectional view of the portal shown in FIG. 2, also including a cold air plenum at its floor.

FIG. 4 is a perspective view of a portal with a clear sliding exit door.

FIG. 5 is a top plan view of a portal with two separate baffle panels for the suppression of external air currants.

DETAILED DESCRIPTION OF THE PREFERRED EMBODIMENTS

Figure 1:
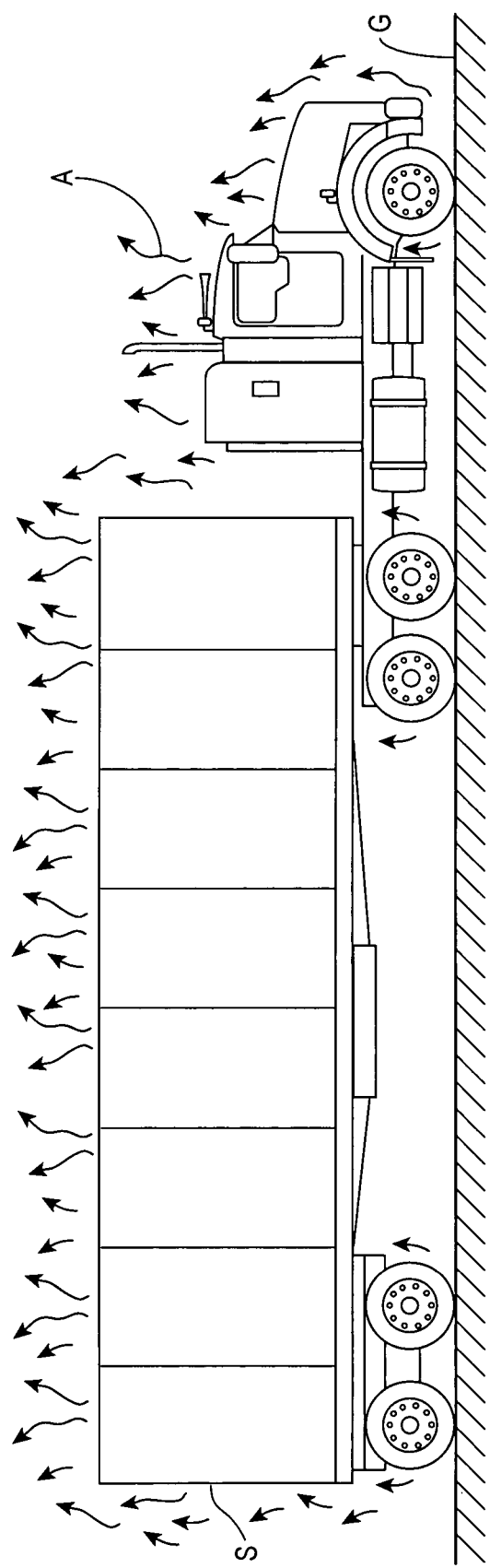
FIG. 1 is a side-elevational view of a vehicular thermal boundary layer and plume.

The portals of the subject invention capitalize on physical phenomena identified by the inventors herein and illustrated schematically in FIG. 1. In particular, FIG. 1 depicts a vehicular subject S standing on a substantially horizontal floor G. The vehicular subject S typically will have a temperature that exceeds the temperature of the ambient air adjacent to the vehicular subject S. The vehicular heat of the vehicular subject S will cause a warming of air adjacent to the vehicular subject S. This warmed air will effectively define a boundary layer of warm air in close proximity to the vehicular subject S. Warm air is less dense than cooler air. As a result, warm air rises relative to cooler air. This known physical phenomenon causes the warm air boundary layer adjacent the vehicular subject S to gradually flow upwardly and through the cooler air at further distances from the vehicular subject S. This upwardly flowing air is identified by arrows "A" in FIG. 1 and collectively defines a vehicular thermal plume.

The vehicular thermal plume cooperates with another physical phenomenon referred to above. In particular, the vehicular subject S continually exchanges microscopic particles and vapors as part of the contaminant exchange process described above. These microscopic particles and vapors are entrained in the upwardly flowing air A that forms the vehicular thermal plume illustrated schematically in FIG. 1.

Figure 2:
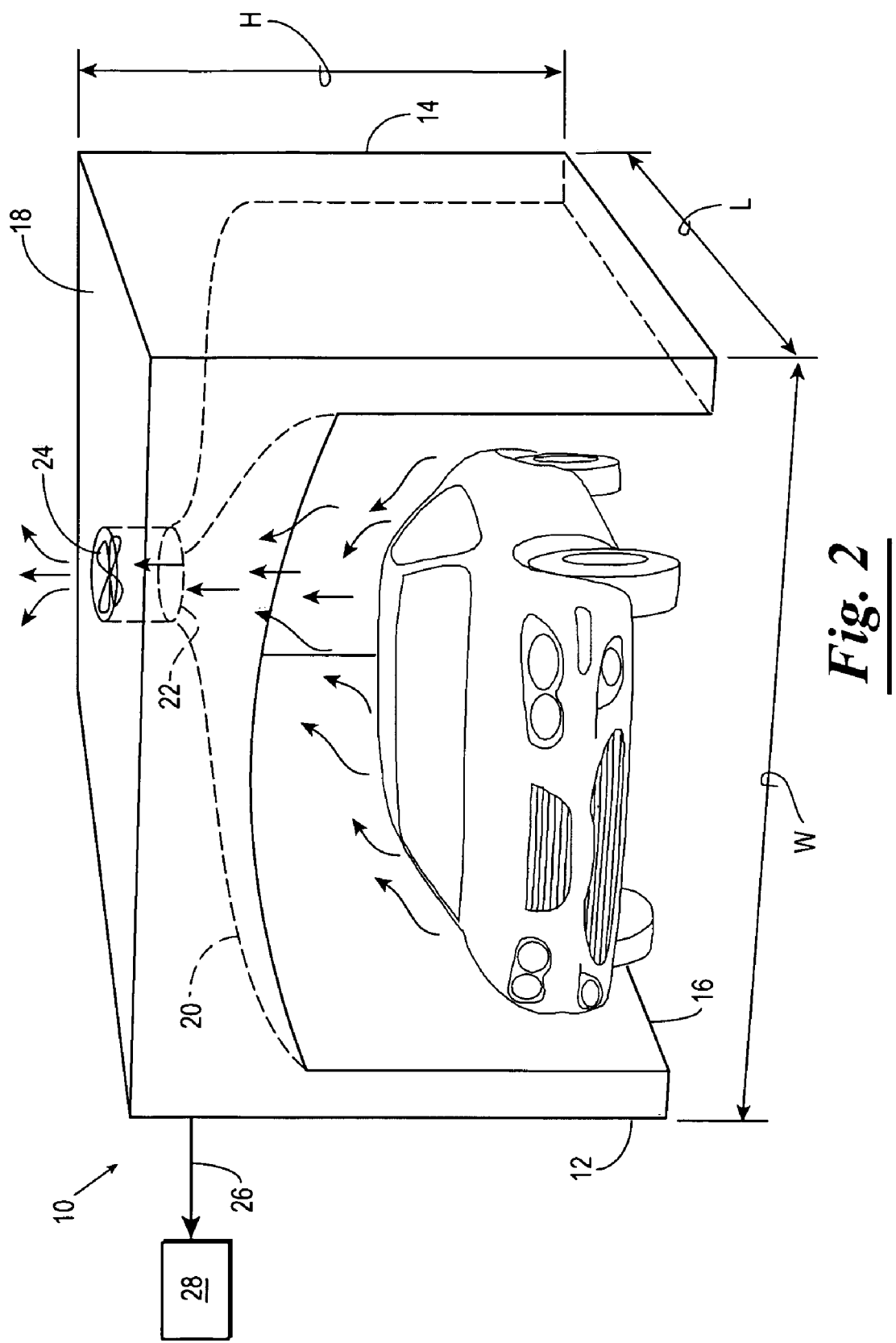
FIG. 2 is a perspective view of a portal in accordance with the subject invention.

A drive-through screening portal for purposes of detection of substances of interest from vehicular subjects, or for the possible collection of human DNA samples, or for the sampling of airborne signals related to the state of mind or health of vehicular-borne subjects, is identified generally by the numeral 10 in FIG. 2. The portal 10 preferably has two substantially vertical sidewalls 12 and 14 that are spaced sufficiently from one another to form an open passage 16 through which a vehicular subject may conveniently pass. Preferably, the sidewalls are spaced from one another to define an overall width "W" of approximately 10 feet for passenger vehicles, 12 feet for cargo vehicles and certain large passenger vehicles, and larger for other, even larger vehicles. Additionally, the sidewalls 12 and 14 define an overall length "L" of approximately 15 feet for passenger vehicles, 60 feet for cargo vehicles and certain large passenger vehicles, and larger for other, even larger vehicles. The portal 10 further has a ceiling 18. The ceiling is disposed above the floor of the portal 10 by a distance sufficient to define an overall internal height "H" of between approximately 7-10 feet for passenger vehicles, 10-15 feet for cargo vehicles and certain large passenger vehicles, and larger for other, even larger vehicles. These dimensions enable most vehicular subjects to pass easily through passage 16 of the portal 10. It is readily recognized by one familiar with the art that for certain vehicles and/or certain applications, the described dimensions may be altered to more readily admit or more closely enclose vehicles of a certain or expected size. Similarly the dimensions may be altered to allow less precise driving into, through, and out of the portal.

The sidewalls 12 and 14 and/or the ceiling 18 may further be provided with alternate detectors comparable to commercially available detectors commonly employed at locations requiring security. Thus, the substances of interest detection functions of the portal 10, as explained herein, may be carried out simultaneously with additional detection functions in an apparatus that is dimensionally comparable to currently employed vehicle screening portals.

Portions of the ceiling 18 that cover the open passage 16 define an inverted contoured funnel 20 that gradually tapers to smaller cross-sectional dimensions at locations further above the passage 16. The funnel 20 is operative to collect the rising thermal plume generated by the vehicle as explained above. The smaller cross-sectional portions of the funnel 20 are provided with a filter, trap or separator identified generally by the numeral 22 in FIG. 2. For ease of reference, the filter, trap or separator 22 will be referred to herein simply by the generic term trap. However, this generic term is not intended to be structurally or functionally limiting. Rather, the trap 22 is any known structure with the ability to extract from the vehicular thermal plume a sample of particulates, such as particles and/or vapor with adsorbed compounds thereon or airborne trace chemical in vapor form. Comparable traps are used in commercially available chemical detectors marketed by Nomadics®, Inc.

A fan 24 or other air circulation generator is provided to generate an airflow that will direct the vehicular thermal plume through the trap 22.

The air drawn through the fan 24 then is expelled to the environment. A conveyor 26 is further provided to present the trap 22 to a substance detector 28 which is schematically illustrated in FIG. 2. Traps and conveyors are known to those skilled in the art. Therefore, no further discussion of traps or conveyors is necessary. As noted above, the substance detector 28 may be a prior art detector, such as one of the detectors shown in U.S. Pat. No. 5,200,614 or U.S. Pat. No. 6,558,626.

As shown in FIG. 3, the portal 10 described above and illustrated in FIG. 2 may be positioned above a floor 30 having a plenum 32 formed therein. The plenum 32 may communicate with the open passage 16 through a plurality of small air apertures 34. The plenum 32 also may communicate with an airflow generator, which is illustrated schematically and identified generally by the numeral 36. The airflow generator 36 may be operative to direct cold air 37 uniformly through the plenum 32, upwardly through the apertures 34 and into the open passage 16 at a speed, desirably no more than approximately 0.5 meter/sec. The flow of cold air 37 at a low speed of no more than 0.5 meter/sec will not function to effectively scrub the vehicular subject and will not add significantly to the volume of air presented to the funnel 20. Rather, the cold air 37 directed through the plenum 32 merely will enhance and speed the natural vertical motion of the warm vehicular thermal plume "A" due to buoyancy effects of the warm boundary layer of air containing the vehicular thermal plume riding above the colder air directed into the passage 16 through the plenum 32. The temperature of the air directed through the plenum preferably should be several degrees cooler than ambient, but need not be so cold as to cause discomfort to the vehicular occupants in the portal 10. An air temperature through the plenum 32 of approximately 60 degrees F. is believed to be sufficient to provide the desired buoyancy effect. In warmer environments, it is clear to one practiced in the art that warmer directed air can be used. Similarly in cooler environments, it is clear to one practiced in the art that cooler directed air is desired so that the directed air is not warmer than the convective column rising from the vehicle and so does not rise faster than the convective column, disturbing the convective column's motion.

An alternate portal is identified generally by the numeral 40 in FIG. 4 and is structurally and functionally similar to the portal 10 described above and illustrated in FIG. 2. The portal 40, however, is provided with a passage 42 having a sliding door 44 at the exit of the passage 42. The door 44 inhibits a through flow of extraneous air 45 that may be attributable to environmental air currents. Additionally, the door 44 provides a more efficient and accurate sequencing of the passage of vehicular subjects through the portal 40, and thereby ensures a more accurate matching of detection data with vehicular subjects. While a horizontally sliding door is shown, the door can be any type of door capable of allowing the passage of a vehicle therethrough. For example, a garage-type door, or even a swinging door. In the preferred embodiment, the door 44 is clear plastic. However, any material capable of inhibiting through flow of extraneous air 45 is acceptable.

The impact of external air currents can be minimized without the provision of a mechanical sliding door as part of the portal. In this regard, FIG. 5 shows the portal 10 of FIG. 2 used in combination with upstream and downstream baffles 46 and 48. The baffles 46 and 48 effectively block a through flow of extraneous air 45 due to wind and other air currents and further contribute to proper sequencing of vehicular subjects through the portal 10 and effective matching of detection data to the respective vehicular subjects. The baffles 46 and 48 preferably are spaced between 6 and 12 feet from the portal 10. However, one familiar with the art will recognize that the baffles must be set back far enough from the portal to permit vehicular subjects to maneuver into and out of the portal. Consequently, in certain applications, for certain vehicles, or for an expectation of a certain range of vehicles, the baffles may require additional spacing away from the portal, or may be moved to permit subject entry and egress and then replaced during screening. While FIG. 5 shows a vehicle entering and leaving from the same side, the vehicle could enter on one side and exit on the other. The baffles 46 and 48 could be canted slightly to allow easier passage of the vehicle, or moved into a different configuration altogether, so long as they effectively block undesirable air flow.

Figure 6:
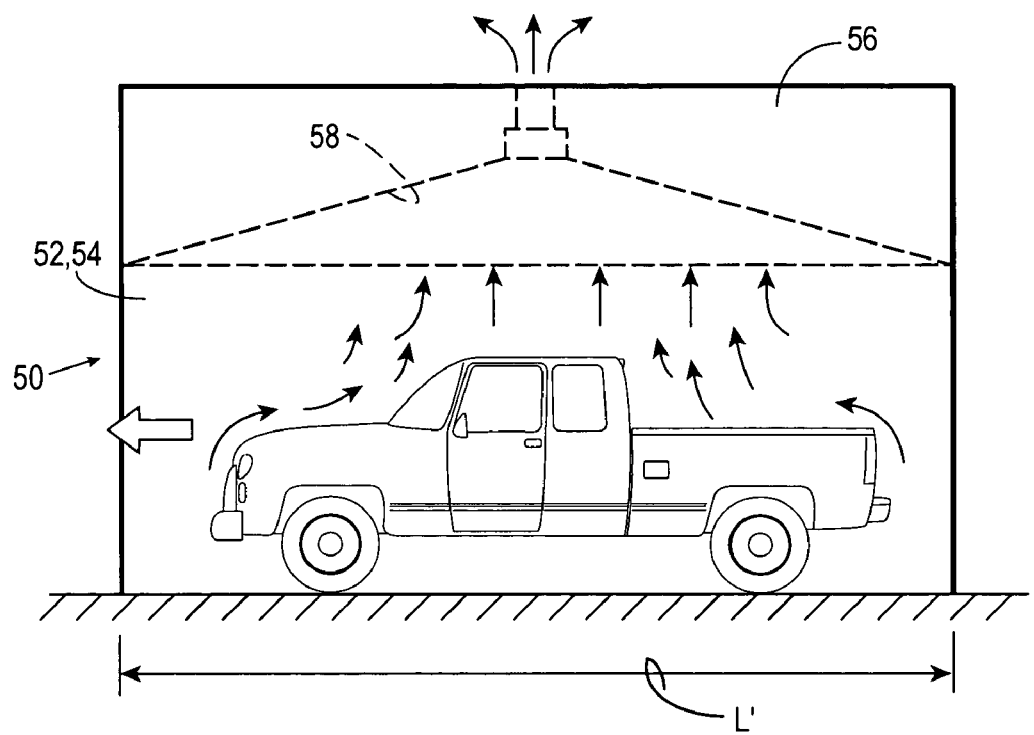
FIG. 6 is an elongated drive-through portal with a ceiling collector.

The portal 10 of the subject invention need not be dimensionally comparable to current commercially available detectors. Rather, FIG. 6 shows an elongated corridor-type of portal that is identified generally by the numeral 50. The corridor portal 50 preferably has a width of approximately 10 feet and a height in the range of 7-10 feet (with similar changes of dimension for larger vehicles as described above for the portal 10), both of which are comparable to the width and height dimensions of the above-described portal 10. However, the portal 50 illustrated in, FIG. 6 preferably has a length L' of approximately 15-40 feet for passenger vehicles, 100-200 feet for cargo vehicles and certain large passenger vehicles, and larger for other, even larger vehicles. Thus, the portal 50 is at least 2-3 times greater in length than the portal 10 described above. The portal 50 may further be provided with sidewalls 52 and 54 formed from a material known to the art, such as concrete or metal. The sidewalls provide a clear indication of the boundary of the corridor of the portal 50. As in the previous embodiments, the portal 50 is provided with a ceiling 56 having an inverted funnel collector 58 formed on interior surfaces thereof. However, the funnel collector 58 of the portal 50 is more elongated.

The placement of windows or cameras in sidewalls 52 and 54 further enable observation of vehicular subjects and their occupants by security personnel working near the portal 50. This ability to observe vehicular subjects and occupants can lead to visual observation of erratic behavior that may justify more detailed searching.

Figure 7:
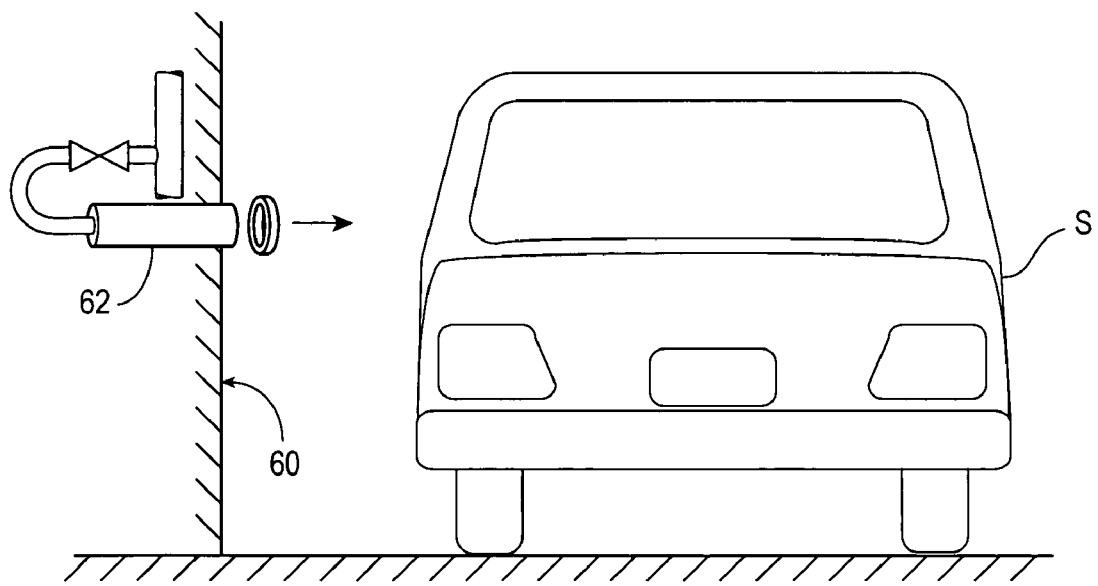
FIG. 7 is a cross-sectional view of a portal employing a vortex-ring impinger.

FIG. 7 is a cross-sectional view of a portal 60 that is structurally and functionally similar or identical to the portals 10, 40 or 50 as described and illustrated above. However, the portal 60 is provided with a vortex-ring generator 62 designed and located to impinge a level of airborne kinetic energy on the surface of vehicular subjects passing therethrough for purposes of agitating said surface to remove trace solids of substances adsorbed thereto. However, the vortex-ring generator 62 provides primarily only a local airflow disturbance and does not significantly alter the natural airflow in the vehicular thermal plume, and does not alter the naturally upward direction of flow of the vehicular thermal plume as illustrated schematically in FIG. 1 above.

Figure 8:
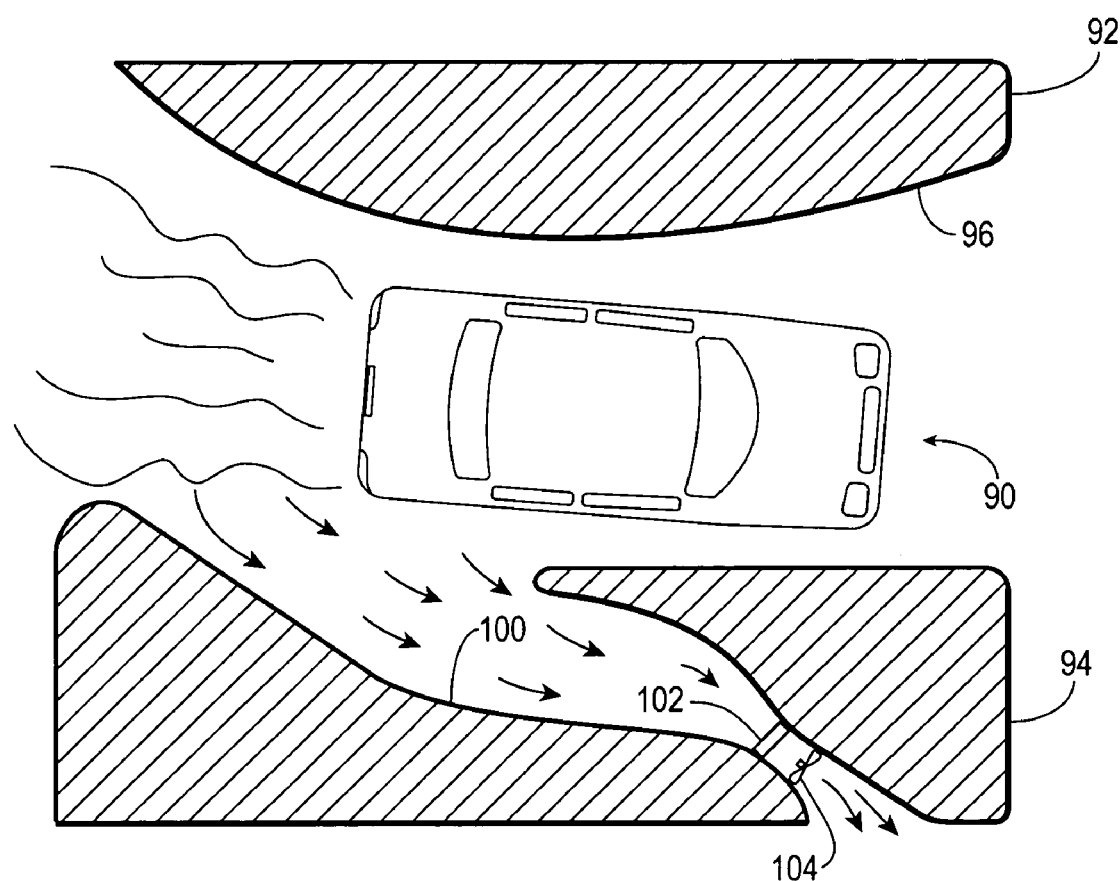
FIG. 8 is a top plan view of a portal to collect a sample from the vehicular thermal wake.

FIG. 8 shows another embodiment of a portal, which is identified generally by the numeral 90. The portal 90 includes first and second spaced apart sidewalls 92 and 94 forming a passage 96 therethrough. In the preferred embodiment, a ceiling extends across the top of the sidewalls 92 and 94. The portal 90 differs from those described above in that it has no funnel-shaped collector in the ceiling. Rather, a funnel-shaped airflow collector 100 is provided on the sidewall 94. The funnel collector 100 is disposed and configured to take advantage of a thermal wake being formed behind a vehicular subject passing through the portal 100. A trap 102 is provided in the narrow portion of the funnel 100 and functions to extract from the vehicular thermal wake either particulates, such as particles and/or vapor with adsorbed compounds thereon, or airborne trace chemicals in vapor form. Thus, the trap 102 is structurally and functionally similar to the trap 22 described with respect to the embodiment of FIG. 2. A blower 104 is provided in proximity to the trap 102 and generates a low speed airflow to draw the vehicular thermal wake through the trap 102 and to expel the remaining airstream to the environment. As in the previous embodiment, the conveyor is provided to present the trapped sample to a substance detector for each vehicular subject passing through the portal 90. As in the previous embodiments, the detector is operative to detect the presence of substances of interest.

While the invention has been described with respect to a preferred embodiment, it is apparent that various changes can be made without departing from the scope of the invention as defined by the appended claims.

What is claimed is:

1. A portal for collecting substances of interest from a vehicular subject passing therethrough, said portal comprising:
   a passage being dimensioned for accommodating passage for the vehicular subject through said portal;
   a ceiling covering said passage, portions of said ceiling adjacent to said passage defining a funnel-shape with a large cross-section adjacent said passage and a smaller cross-section at locations further from said passage;
   a collector for collecting air from the vehicular subject as a plume or wake from the vehicular subject through the portion of the ceiling having the smaller cross-section, said collector being operative for accommodating the air in the plume or wake; and
   a detector capable of receiving and analyzing one or more samples of said air and providing an indication of the content of the samples.

2. The portal of claim 1, wherein portions of said ceiling adjacent to said passage define said collector.

3. The portal of claim 1, further comprising a plurality of sidewalls spaced from one another.

4. The portal of claim 3, wherein at least one of said sidewalls is formed from a transparent material.

5. The portal of claim 3, wherein said sidewalls are spaced from one another by a selected distance, each said sidewall defining a length substantially greater than said distance between said sidewalls.

6. The portal of claim 3, further comprising at least one vortex tube mounted to at least one said sidewall, said vortex tube having a first end communicating with said passage through said portal and a second end spaced from said passage, a supply of compressed air communicating with said second end of said vortex tube for selectively producing a vortex ring for delivering airborne kinetic energy to the vehicular subject passing through said portal sufficient to agitate the surface of said vehicular subject and liberate trace solids of substances adsorbed thereto without significantly altering the natural airflow adjacent said vehicular subject.

7. The portal of claim 3, wherein portions of said sidewall adjacent to said passage define said collector.

8. The portal of claim 1, further comprising a trap removably positioned in the collector, said trap being selected from a material for permitting passage of air therethrough but for trapping particulates and substances of interest in said air.

9. The portal of claim 8, further comprising a conveyor for periodically transferring said trap to said detector.

10. The portal of claim 1, further comprising at least one baffle spaced externally of said passage a sufficient distance to enable a vehicular subject to enter and leave said passage of said portal, said baffle being dimensioned to substantially block external air currents from entering said portal.

11. The portal of claim 1, further comprising a selectively openable door for impeding flow of external air currents through said portal.

12. The portal of claim 1, wherein the collector has an air circulation generator.

13. The portal of claim 1, further comprising a plenum, said plenum being in communication with a supply of cool air at a temperature cooler than ambient air, a blower for directing said cool air from said plenum into said passage, said cool air from said plenum buoyantly enabling warm air adjacent said vehicular subject to rise toward said collector.

14. The portal of claim 13, wherein said blower is operative to direct said cool air at a speed of no more than approximately 0.5 meters/sec.

15. The portal of claim 13, wherein said cool air has a temperature lower than the ambient temperature.

16. The portal of claim 13, wherein said cool air has a temperature of about 60 degrees F.

17. A method for collecting substances of interest from a vehicular subject, said method comprising the steps of:
providing a portal with a passage being dimensioned for accommodating passage for the vehicular subject through said portal, a collector for collecting air from the vehicular subject as a plume or wake from the vehicular subject, said collector being operative for accommodating the air in the plume or wake, a ceiling covering said passage, portions of said ceiling adjacent to said passage defining a funnel-shape with a large cross-section adjacent said passage and a smaller cross-section at locations further from said passage, and a detector capable of receiving and analyzing one or more samples of said air through the portion of the ceiling having the smaller cross-section and providing an indication of the content of the samples;
allowing said vehicular subject into said passage such that the plume or wake air from said vehicular subject exists in said passage, said air in said plume or wake rising in proximity to said vehicular subject in said passage; and
receiving one or more samples of said air from said plume or wake in said collector.

18. The method of claim 17, wherein the portal further comprises a trap removably positioned in the collector, said trap being selected from a material for permitting passage of air therethrough, but for trapping particulates and substances of interest in said air, and a conveyor for periodically transferring said trap to said detector; further comprising the step of transferring said trap to said detector.

19. The method of claim 17, further comprising the step of detecting substances of interest within the plume or wake in said collector.

20. The method of claim 17, wherein the portal further comprises:
a plurality of sidewalls spaced from one another, wherein at least one vortex tube mounted to at least one said sidewall, said vortex tube having a first end communicating with said passage through said portal and a second end spaced from said passage, a supply of compressed air communicating with said second end of said vortex tube for selectively producing a vortex ring for delivering airborne kinetic energy to the vehicular subject passing through said portal sufficient to agitate the surface of said vehicular subject and liberate trace solids of substances adsorbed thereto without significantly altering the natural airflow adjacent said vehicular subject; further comprising the step of activating said vortex tube.

21. The method of claim 17, wherein the portal further comprises a selectively openable door for impeding flow of external air currents through said portal; and further comprising the step of opening said door.

22. The method of claim 17, wherein the portal further comprises a selectively openable door for impeding flow of external air currents through said portal; and further comprising the step of closing said door.

23. The method of claim 17, wherein said collector has an air circulation generator; and further comprising the step of activating said air circulation generator.

24. The method of claim 17, wherein the portal further comprises a plenum, said plenum being in communication with a supply of cool air at a temperature cooler than ambient air, a blower for directing said cool air from said plenum into said passage, said cool air from said plenum buoyantly enabling warm air adjacent said vehicular subject to rise toward said collector; and further comprising the step of activating said blower.

* * * * *